United States Patent
Karlson et al.

(10) Patent No.: US 9,271,880 B2
(45) Date of Patent: Mar. 1, 2016

(54) ABSORBENT ARTICLE COMPRISING AN ELASTIC WEB MATERIAL

(75) Inventors: Tomas Karlson, Savedalen (SE); Anders Gustafsson, Billdal (SE); Urban Widlund, Pixbo (SE); Jan Wastlund-Karlsson, Molndal (SE); Margareta Wennerback, Molnlycke (SE)

(73) Assignee: SCA HYGIENE PRODUCTS AB, Gothenburg (SE)

( * ) Notice: Subject to any disclaimer, the term of this patent is extended or adjusted under 35 U.S.C. 154(b) by 2520 days.

(21) Appl. No.: 11/576,497

(22) PCT Filed: Oct. 4, 2004

(86) PCT No.: PCT/SE2004/001415
§ 371 (c)(1), (2), (4) Date: Dec. 3, 2008

(87) PCT Pub. No.: WO2006/038837
PCT Pub. Date: Apr. 13, 2006

(65) Prior Publication Data
US 2011/0144610 A1   Jun. 16, 2011

(51) Int. Cl.
*A61F 13/514* (2006.01)

(52) U.S. Cl.
CPC ....... *A61F 13/51464* (2013.01); *A61F 13/5146* (2013.01); *A61F 13/5148* (2013.01);
(Continued)

(58) Field of Classification Search
CPC ............ A61F 13/51464; A61F 13/51401; A61F 13/5146; A61F 13/51462; A61F 13/5148; A61F 13/51484

USPC ............ 604/367, 372, 385.14, 385.22, 604/385.24–385.27, 385.3
See application file for complete search history.

(56) References Cited

U.S. PATENT DOCUMENTS 3,259,539 A *  7/1966  Katz et al. ............ 162/146
3,424,162 A     1/1969  Parravicini
(Continued)

FOREIGN PATENT DOCUMENTS

CO   2007-0003796      1/2008
EP   0 287 388 A2     10/1988
(Continued)

OTHER PUBLICATIONS

An English Translation of the Notice of Reasons for Rejection issued in the corresponding Japanese Patent Application No. 2007-517994 dated Nov. 24, 2009.
(Continued)

*Primary Examiner* — Lynne Anderson
*Assistant Examiner* — Kathryn E Ditmer
(74) *Attorney, Agent, or Firm* — Buchanan Ingersoll & Rooney PC

(57) ABSTRACT

A pant type absorbent article such as a pant diaper, a sanitary pant or incontinence pant, said article having a core region (3) comprising an absorbent core (2) and a chassis region (4) surrounding the core region. The chassis comprises front, back and waist regions (5, 6 and 7). The article in at least a part of the chassis region (4) comprises an outer coversheet (10) in the form of an elastic web material (11) constituting the sole component of the chassis (4) in at least 20% of the total surface area of the article (1), said elastic laminate having an opacity of at least 40% and a basis weight of no more than 100 g/m$^2$.

41 Claims, 2 Drawing Sheets

(52) U.S. Cl.
CPC ..... *A61F13/51401* (2013.01); *A61F 13/51462* (2013.01); *A61F 13/51484* (2013.01); *A61F 13/51496* (2013.01)

(56) References Cited

U.S. PATENT DOCUMENTS

| | | | |
|---|---|---|---|
| 4,119,450 A | 10/1978 | Bianco | |
| 4,663,220 A | 5/1987 | Wisneski et al. | |
| 4,698,261 A | 10/1987 | Bothe | |
| 4,739,012 A | 4/1988 | Hagman | |
| 4,777,080 A | 10/1988 | Harris, Jr. et al. | |
| 4,842,596 A | 6/1989 | Kielpikowski et al. | |
| 4,850,990 A * | 7/1989 | Huntoon et al. | 604/385.22 |
| 4,932,949 A | 6/1990 | Thygesen et al. | |
| 5,114,781 A | 5/1992 | Morman | |
| 5,143,679 A | 9/1992 | Weber et al. | |
| 5,156,793 A | 10/1992 | Buell et al. | |
| 5,167,897 A | 12/1992 | Weber et al. | |
| 5,261,899 A | 11/1993 | Visscher et al. | |
| 5,336,545 A | 8/1994 | Morman | |
| 5,422,172 A | 6/1995 | Wu | |
| 5,440,764 A | 8/1995 | Matsushita | |
| 5,462,541 A | 10/1995 | Bruemmer et al. | |
| 5,514,470 A | 5/1996 | Haffner et al. | |
| 5,592,690 A | 1/1997 | Wu | |
| 5,628,738 A | 5/1997 | Suekane | |
| 5,634,216 A | 6/1997 | Wu | |
| 5,635,290 A | 6/1997 | Stopper et al. | |
| 5,706,524 A | 1/1998 | Herrin et al. | |
| 5,733,628 A | 3/1998 | Pelkie | |
| 5,746,730 A | 5/1998 | Suzuki et al. | |
| 5,769,838 A | 6/1998 | Buell et al. | |
| 5,861,074 A | 1/1999 | Wu | |
| 5,921,973 A | 7/1999 | Newkirk et al. | |
| 6,072,005 A | 6/2000 | Kobylivker et al. | |
| 6,106,925 A | 8/2000 | Palumbo | |
| 6,210,386 B1 | 4/2001 | Inoue | |
| 6,240,569 B1 | 6/2001 | van Gompel et al. | |
| 6,476,289 B1 | 11/2002 | Buell | |
| 6,540,731 B2 | 4/2003 | Magnusson et al. | |
| 6,552,245 B1 | 4/2003 | Roessler | |
| 6,585,713 B1 | 7/2003 | LeMahieu et al. | |
| 6,627,564 B1 | 9/2003 | Morman et al. | |
| 6,914,018 B1 | 7/2005 | Uitenbroek et al. | |
| 7,722,591 B2 | 5/2010 | Back | |
| 2002/0002021 A1 | 1/2002 | May et al. | |
| 2002/0004350 A1* | 1/2002 | Morman et al. | 442/381 |
| 2002/0019187 A1* | 2/2002 | Carroll et al. | 442/394 |
| 2002/0029026 A1 | 3/2002 | Furuya et al. | |
| 2002/0052591 A1 | 5/2002 | Zehner et al. | |
| 2003/0022582 A1 | 1/2003 | Cree | |
| 2003/0078558 A1 | 4/2003 | Karami et al. | |
| 2003/0088230 A1* | 5/2003 | Balogh et al. | 604/385.101 |
| 2003/0124310 A1* | 7/2003 | Ellis et al. | 428/138 |
| 2003/0135184 A1* | 7/2003 | Van Gompel et al. | 604/385.01 |
| 2004/0078018 A1 | 4/2004 | Van Gompel et al. | |
| 2004/0102746 A1 | 5/2004 | Mortell et al. | |
| 2004/0116887 A1 | 6/2004 | Thorson et al. | |
| 2004/0122405 A1 | 6/2004 | Van Gompel et al. | |
| 2004/0122406 A1 | 6/2004 | Moser et al. | |
| 2004/0127878 A1 | 7/2004 | Olson et al. | |
| 2004/0133180 A1 | 7/2004 | Mori et al. | |
| 2004/0192140 A1 | 9/2004 | Schneider et al. | |
| 2004/0197588 A1 | 10/2004 | Thomas et al. | |
| 2004/0241389 A1 | 12/2004 | Chung et al. | |
| 2004/0243086 A1* | 12/2004 | VanGompel et al. | 604/385.3 |
| 2005/0010186 A1 | 1/2005 | Otsubo et al. | |
| 2005/0101216 A1 | 5/2005 | Middlesworth et al. | |
| 2005/0106980 A1 | 5/2005 | Abed et al. | |
| 2005/0133151 A1* | 6/2005 | Maldonado Pacheco et al. | 156/164 |
| 2006/0148358 A1 | 7/2006 | Hall et al. | |
| 2007/0233034 A1 | 10/2007 | Hildeberg et al. | |
| 2008/0000003 A1 | 1/2008 | Melander | |
| 2008/0033387 A1 | 2/2008 | Wastlund-Karlsson et al. | |
| 2010/0036355 A1 | 2/2010 | Hakansson et al. | |

FOREIGN PATENT DOCUMENTS

| | | |
|---|---|---|
| EP | 0 304 957 A2 | 3/1989 |
| EP | 0 360 929 A1 | 4/1990 |
| EP | 0 409 307 B1 | 1/1991 |
| EP | 0 418 493 A1 | 3/1991 |
| EP | 0 861 647 A2 | 9/1998 |
| EP | 0 714 351 B1 | 12/1998 |
| EP | 0 605 012 B1 | 3/1999 |
| EP | 0 604 731 B1 | 6/1999 |
| EP | 1 184 022 A2 | 3/2002 |
| EP | 1 035 818 B1 | 4/2002 |
| EP | 1 384 459 A2 | 1/2004 |
| EP | 1 473 008 A1 | 11/2004 |
| FR | 2 586 558 | 3/1987 |
| FR | 2 810 879 | 1/2002 |
| GB | 2 284 538 A | 6/1995 |
| JP | 06255006 A | 9/1994 |
| JP | 07-252762 | 10/1995 |
| JP | 09-286085 | 11/1997 |
| JP | 10043235 | 2/1998 |
| JP | H11-276523 | 10/1999 |
| JP | 2002 058 703 | 2/2002 |
| JP | 2002-065740 | 3/2002 |
| JP | 2002-172137 A | 6/2002 |
| JP | 2002-520090 T | 7/2002 |
| JP | 2002-273808 A | 9/2002 |
| JP | 2003-520146 | 7/2003 |
| JP | 2003-290284 A | 10/2003 |
| JP | 2004-050621 A | 2/2004 |
| JP | 2004-098356 A | 4/2004 |
| JP | 2004-519270 | 7/2004 |
| JP | 2005-511345 A | 4/2005 |
| JP | 2006-511274 A | 4/2006 |
| RU | 2 008 774 | 3/1994 |
| RU | 2 221 531 | 1/2004 |
| SU | 965339 | 10/1982 |
| SU | 965339 A | 10/1982 |
| TW | 233473 | 11/1994 |
| WO | WO 95/19258 | 7/1995 |
| WO | WO 96/10979 A1 | 4/1996 |
| WO | WO 97/29722 A1 | 8/1997 |
| WO | WO 97/34037 A1 | 9/1997 |
| WO | WO 98/37847 A1 | 9/1998 |
| WO | WO 99/27876 A1 | 6/1999 |
| WO | 99/32164 | 7/1999 |
| WO | WO 00/02511 A1 | 1/2000 |
| WO | WO 00/45764 A1 | 8/2000 |
| WO | WO 01/30563 A1 | 5/2001 |
| WO | WO 01/45927 A1 | 6/2001 |
| WO | WO 01/53076 | 7/2001 |
| WO | WO 02/34185 | 5/2002 |
| WO | WO 02/49560 A1 | 6/2002 |
| WO | WO 03/004748 A1 | 1/2003 |
| WO | 03/019714 | 3/2003 |
| WO | 03/047488 | 6/2003 |
| WO | WO 03/047488 A1 | 6/2003 |
| WO | WO 2004/058120 | 7/2004 |
| WO | WO 2004/060251 A1 | 7/2004 |
| WO | WO 2004/078083 A1 | 9/2004 |
| WO | WO 2005/095700 | 10/2005 |
| WO | 2005/122984 | 12/2005 |
| WO | 2005/122985 | 12/2005 |
| WO | WO 2006/038837 A1 | 4/2006 |
| WO | WO 2006/093443 A1 | 4/2006 |
| WO | WO 2006/093439 A1 | 9/2006 |
| WO | WO 2006/093440 A1 | 9/2006 |
| WO | WO 2007/114744 A1 | 10/2007 |
| WO | WO 2008/060194 A1 | 5/2008 |

OTHER PUBLICATIONS

An English Translation of the Notice of Reasons for Rejection issued in the corresponding Japanese Patent Application No. 2007-534537 dated Jan. 26, 2010.

(56) References Cited

OTHER PUBLICATIONS

Office Action dated May 26, 2010, issued in the corresponding Australian Patent Application No. 2004323904.

Hildeberg et. al, Copending U.S. Appl. No. 11/630,371, filed Dec. 21, 2006 entitled "Absorbent Article Comprising an Elastic Laminate Material".

Wastlund-Karlssson et al., Copending U.S. Appl. No. 11/630,372, filed Dec. 21, 2006 entitled "Absorbent Article Comprising an Elastic Laminate".

Melander, Copending U.S. Appl. No. 11/845,153, filed Aug. 27, 2007 entitled "Underwear Article Comprising an Elastic Laminate".

Wennerback, Copending U.S. Appl. No. 12/446,297, filed Apr. 20, 2009 entitled "Absorbent Article Comprising an Elastic Laminate".

Norrby et al., Copending U.S. Appl. No. 12/447,694, filed Apr. 29, 2009 entitled "Elastic Laminate and Absorbent Article Comprising the Laminate".

Wennerback, Copending U.S. Appl. No. 12/514,086, filed May 8, 2009 entitled "Absorbent Article Comprising an Elastic Laminate Material".

Non-Final Office Action in Copending U.S. Appl. No. 11/630,372 to Wastlund-Karlson et al. dated Sep. 16, 2009.

Final Office Action in Copending U.S. Appl. No. 11/630,372 to Wastlund-Karlson et al. dated Mar. 2, 2008.

Non-Final Office Action in Copending U.S. Appl. No. 11/630,372 to Wastlund-Karlson et al. dated Jul. 8, 2009.

Non-Final Office Action in Copending U.S. Appl. No. 11/630,371 to Hildeberg et al. dated Oct. 5, 2009.

Sueo Kawabata, "The Standardization and Analysis of Hand Evaluation", Second Edition, The Hand Evaluation and Standardization Committee, The Textile Machinery Society of Japan, published by The Textile Machinery Society of Japan, Osaka, Japan, Jul. 1980—Textile Machinery Japan.

English version of Office Inquiry issued on Oct. 11, 2011, in corresponding Japanese Patent Application No. 2007-534537.

Notice of Reasons for Rejection issued on Jun. 12, 2012, in corresponding Japanese Patent Application No. 2007-534537, and an English translation thereof.

\* cited by examiner

ABSORBENT ARTICLE COMPRISING AN ELASTIC WEB MATERIAL

TECHNICAL FIELD

The present invention refers to a pant type absorbent article such as a pant diaper, a sanitary pant or incontinence garment, said article comprising an elastic web material.

BACKGROUND OF THE INVENTION

Absorbent articles having defined core regions and chassis regions are supposed to have a comfortable fit about the wearer. For pant articles like pant diapers, sanitary pants and incontinence pants it is also desirable that the articles are capable of being pulled up and down over the hips of the wearer to allow the wearer or caregiver to easily put on and remove the article when it has been soiled. It is known to make such absorbent pants with elasticized stretchable side panels and waist portion, usually comprising elastic members, such as elastic threads, contractably affixed between the backsheet and the topsheet.

It is further known to make portions of the chassis of absorbent articles of an elastic material, such as stretch-bonded laminates. Such laminates may include a layer of meltblown elastomeric fibers which have been stretched and sandwiched between outer layers of spunbonded webs.

U.S. Pat. No. 6,552,245 discloses an extensible outer cover for an absorbent article which provides a certain permanent deformation when subjected to a tensile force. The extensible outer cover comprises a necked laminate in the form of one layer of a necked non-elastic film and one layer of an elastic film. The films may be breathable.

WO 03/047488 discloses an elastic laminate comprising an elastic film which on opposite sides is bonded to first and second non-elastic fibrous layers. The laminate is made by bonding the non-elastic fibrous layers to the elastic film layer and subsequently stretching the composite material, causing the non-elastic materials to break. The elastic film material may be of a breathable material. The laminate may be incorporated in an absorbent article.

US2003/0022582 describes a laminate in which an elastomeric film is bound between two or more layers of nonwoven webs. The laminate is said to be particularly useful in elastic diaper "ears" that can be stretched to accommodate variously sized wearers.

Further examples of absorbent articles which in part are made of elastic laminates are found in U.S. Pat. No. 6,476,289 and JP 10043235.

WO03/19714 discloses a polymeric multilayer film having a high percentage of fillers. U.S. Pat. No. 4,698,261 describes an opaque polyolefin film comprising five layers which is advantageously used for packaging purposes. WO99/32164 describes disposable absorbent articles comprising a microporous backsheet upon which graphics can be printed. The backsheet of WO99/32164 is advantageously whitened with additives.

International applications PCT/SE2004/001004 and PCT/SE2004/001005 refer to absorbent articles comprising an outer coversheet in the form of an elastic laminate having improved cloth-like feel and puncture resistance.

There is however still room for improvement with respect to the properties of absorbent articles comprising an elastic web material, for example an elastic laminate, as an outer coversheet, particularly their cloth-like appearance. The comfort, fit and soft feel of absorbent articles of the above mentioned type is also important. The cost aspect is further important for disposable articles, which are discarded after one single use.

OBJECT AND SUMMARY

An object of the present invention is to provide an absorbent article having a core region and a chassis region and which combines properties of comfort and fit to the wearer's body and a soft and cloth-like appearance and feel close to textile materials.

The article has a core region comprising an absorbent core and a chassis region surrounding the core region, said chassis region comprising front, back and waist regions, while the core region is located at least in the crotch portion of the article, a liquid impermeable backsheet is arranged at least in the core region on the garment facing side of the absorbent core and a liquid permeable topsheet is arranged at least in the core region on the wearer-facing side of the absorbent core. In at least a part of the chassis region the article comprises an outer coversheet in the form of an elastic web material constituting the sole component of the chassis in at least 20% of the total surface area of the article, said elastic web material having an opacity of at least 40% and a basis weight of no more than 100 g/m².

Preferably the elastic web material has an opacity of at least 50%, more preferably at least 60%.

In one embodiment the elastic web material is a laminate composed of first and second layers of fibrous material and an elastic film layer located between said first and second fibrous layers, In one aspect of the invention the elastic film contains an opacifying filler.

According to one embodiment the opacifying filler is an organic or inorganic dye, a coloring agent or a whitening agent. Materials such as titanium dioxide, inorganic carbonates, synthetic carbonates, talc, nepheline syenite, magnesium hydroxide, aluminium trihydrate siatomaceous earth, mica, natural or synthetic silicas, calcinated clays and mixtures thereof are examples of suitable opacifying fillers.

In one embodiment, both layers of fibrous material of the elastic laminate have an elongation at maximum load greater than the elasticity of the elastic laminate.

Characteristically, the layers of fibrous material have an elongation at maximum load of at least 10%, preferably at least 20% greater than the elasticity of the elastic laminate.

In a further embodiment the elastic film layer is breathable.

In one aspect of the invention the elastic laminate has a Water Vapour Transmission Rate according to ASTM E96-00 Procedure D of at least 1500 g/m² 24 h, preferably at least 3000 g/m² 24 h.

In yet a further embodiment, the first and/or the second layers of fibrous material comprise a mixture of polypropylene and polyethylene polymers.

According to one embodiment said elastic laminate comprises first and second fibrous layers of spunbond material, each having a basis weight of between 10 and 35 g/m², preferably between 12 and 30 g/m², more preferably between 10 and 25 g/m², and a breathable elastic film layer having a basis weight between 20 and 80 g/m², preferably between 20 and 60 g/m², said elastic laminate having a Water Vapour Transmission Rate according to ASTM E96-00 Procedure D of at least 1500 g/m² 24 h, preferably at least 3000 g/m² 24 h.

According to a further embodiment said elastic web material has an elasticity in the transverse direction of the article of at least 30%, preferably at least 50%, more preferably at least 70%, when measured according to the elasticity test specified in the description.

In one aspect of the invention the elastic web material has a basis weight of no more than 90 g/m².

In a further aspect the elastic web material has an opacity (%)/basis weight (g/m²) ratio of at least 0.4, preferably at least 0.5 and more preferably at least 0.6.

According to a further embodiment the elastic web material constitutes the sole component of the chassis in at least 25%, preferably at least 30%, more preferably at least 40%, of the surface area of the article.

In one aspect of the invention said elastic web material has a Softness (5) according to Kawabata of at least 20, preferably at least 30 and more preferably at least 40.

According to one embodiment said elastic web material has a Formability (F) according to Kawabata of no more than 50, preferably no more than 30, more preferably no more than 20 and most preferably no more than 10.

In a further embodiment said elastic web material has a Drapability (D) according to Kawabata of no more than 40.

According to a further embodiment a substantial part of the crotch portion of the article is free from said elastic web material.

For certain applications it is preferred that the waist region of the chassis region is free from said elastic web material.

According to one embodiment the surface area of the absorbent core amounts to no more than 30%, preferably not more than 20%, of the total surface area of the article, as measured in a flat state of the article. The term "flat state" herein means in an opened untensioned state, as seen in FIG. 2 of the drawings, and in which any tensioned elastic members have been deactivated.

In one embodiment of the invention the elastic web material constitutes both the outer and the inner coversheet of the article in at least a part of the chassis region.

In a further aspect of the invention the article is a pull-up pant product comprising an elastic waist region, which is free from said elastic web material, a crotch portion which is also free from said elastic web material and wherein the elastic web material is arranged as the sole component in at least a substantial part of the front region of the article, which in use is intended to be applied over the stomach of the wearer. The term "a substantial part" herein means at least 50% of the surface area of the front region.

DESCRIPTION OF PREFERRED EMBODIMENTS

Figure 1:
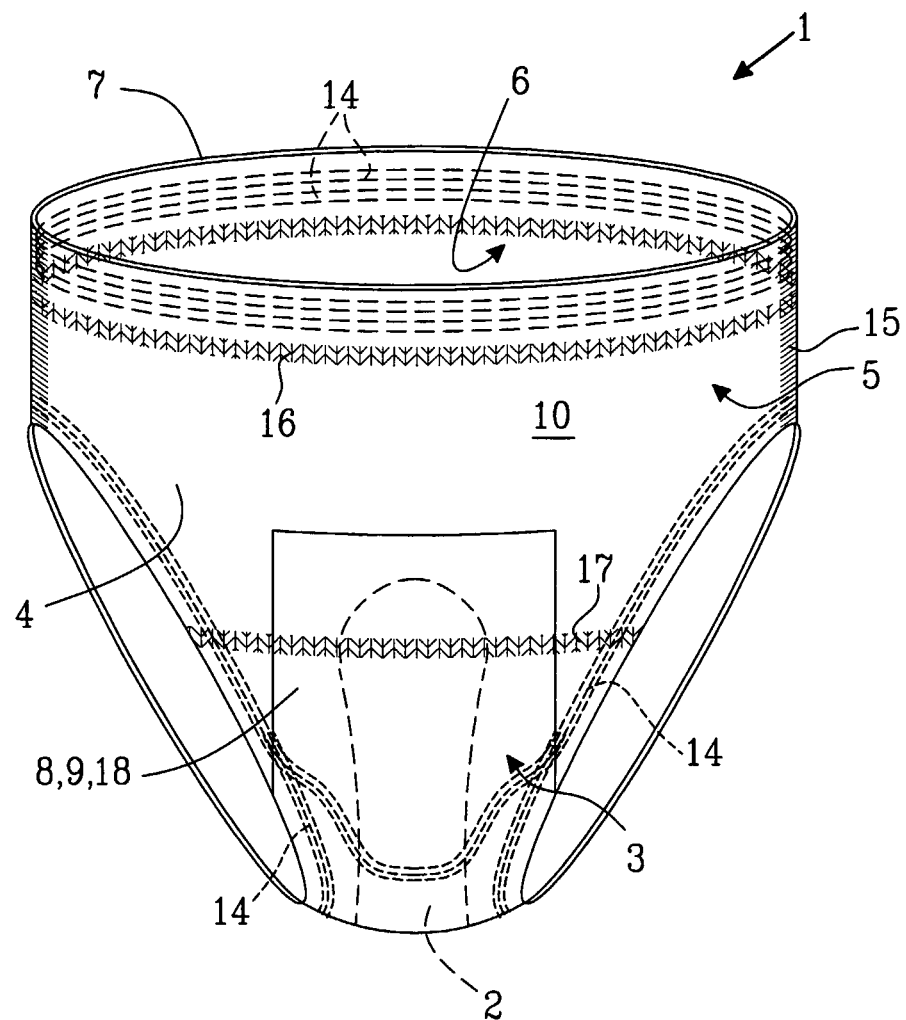
FIG. 1 shows a perspective view of a pant diaper.

The invention will in the following be closer described with reference to some embodiments shown in the accompanying drawings.

Absorbent Article

The term "absorbent article" refers to products that are placed against the skin of the wearer to absorb and contain body exudates, like urine, faeces and menstrual fluid. The invention mainly refers to disposable absorbent articles, which means articles that are not intended to be laundered or otherwise restored or reused as an absorbent article after use. According to the invention pant type absorbent articles are referred to having a core region and a chassis region surrounding the core region. Examples of such pant type absorbent articles are pant diapers, sanitary pants and incontinence pants.

The drawings show an embodiment of a pant diaper 1 for an infant or an incontinent adult. Said pant diaper typically comprises an absorbent core 2 located in a core region 3 of the article, and a chassis 4 surrounding the core region. The chassis comprises front 5, back 6 and waist regions 7. The core region 3 is located at least in the crotch portion 19 of the article and extends a certain distance into the front 5 and back regions 6. The crotch portion 19 is herewith defined as the narrow part of the article intended to be worn in the wearer's crotch between the legs.

The article has a longitudinal direction y and a transverse direction x.

The article comprises a liquid permeable topsheet 8 and a liquid impermeable backsheet 9 covering at least the core region 3. The absorbent core 2 is enclosed between the topsheet and the backsheet.

Topsheet

The liquid permeable topsheet 8 can consist of a nonwoven material, e g spunbond, meltblown, carded, hydroentangled, wetlaid etc. Suitable nonwoven materials can be composed of natural fibers, such as woodpulp or cotton fibres, manmade fibres, such as polyester, polyethylene, polypropylene, viscose etc. or from a mixture of natural and manmade fibres. The topsheet material may further be composed of tow fibres, which may be bonded to each other in a bonding pattern, as e.g. disclosed in EP-A-1 035 818. Further examples of topsheet materials are porous foams, apertured plastic films etc. The materials suited as topsheet materials should be soft and non-irritating to the skin and intended to be readily penetrated by body fluid, e.g. urine or menstrual fluid. The topsheet may be different in different parts of the absorbent article.

Backsheet

The liquid impervious backsheet 9 covering the core region 3 on the garment-facing side of the core is of a liquid impervious material, such as a thin plastic film, e.g. a polyethylene or polypropylene film, a nonwoven material coated with a liquid impervious material, a hydrophobic nonwoven material, which resists liquid penetration or a laminate comprising plastic films and nonwoven materials. The core region backsheet material 9 may be breathable so as to allow vapour to escape from the absorbent core, while still preventing liquids from passing therethrough. Examples of breathable backsheet materials are porous polymeric films, nonwoven laminates from spunbond and meltblown layers, laminates from porous polymeric films and nonwovens. The backsheet 9 is preferably inelastic.

Outer Coversheet

The outer coversheet 10 covering the front and back regions 5 and 6 of the chassis 4 comprises an elastic web material 11 having a basis weight of no more than 100 g/m². The elastic web material is elastic at least in the transverse x-direction of the article. The elasticity in the x-direction should be at least 30%, preferably at least 50%, more preferably at least 70%, as measured by the elasticity test specified below.

Preferably the elastic web material is elastic also in the y-direction of the article. However the elasticity in the y-direction is preferably lower than in the x-direction. The elasticity in the y-direction should in be at least 20%.

In the embodiment shown and described below the elastic web material is an elastic laminate 11 is composed of first and second outer layers of fibrous material 12a and 12b and a middle elastic film layer 13 located between said fibrous layers. However it is understood that other types of elastic web materials may be used, such as elastic nonwoven materials, nonwoven materials which per se are inelastic, but which have been elastified by means of elastic threads etc. The elastic web materials may comprise one layer or two or more layers that have been laminated.

In the elastic laminate shown and described below it is preferred that the outer fibrous layers 12a and 12b are chosen so that they, in combination with the inner elastic film layer, give the material high resistance to puncture. They also provide a soft and cloth-like feel to the laminate. Examples of suitable materials are carded webs and spunbond materials. The basis weight of the fibrous material layers should be between 10 and 35 $g/m^2$, preferably between 12 and 30 $g/m^2$, more preferably between 15 and 25 $g/m^2$. Examples of suitable polymers used in the fibrous materials are polyethylene, polyesters, polypropylene and other polyolefin homopolymers and copolymers. Natural fibres, for example cotton, may also be used as long as they provide the required properties. A mixture of polymers can contribute to a higher flexibility of the nonwoven layer, and through this, give the nonwoven material a higher elongation at maximum load. A mixture of polyethylene and polypropylene polymers has proved to provide good results in this respect. A mixture of fibers of different polymers is also possible.

The middle layer is according to one embodiment of the invention an apertured elastic film having a basis weight between 20 and 80 $g/m^2$, preferably between 20 and 60 $g/m^2$. The film may be of any suitable elastic polymer, natural or synthetic. Some examples of suitable materials for the elastic film are low crystallinity polyethylenes, metallocene-catalyzed low crystallinity polyethylene, ethylene vinyl acetate copolymers (EVA), polyurethane, polyisoprene, butadiene-styrene copolymers, styrene block copolymers, such as styrene/isoprene/styrene (SIS), styrene/butadiene/styrene (SBS), or styrene/ethylene-butadiene/styrene block copolymer. Blends of these polymers may also be used as well as other modifying elastomeric or non-elastomeric materials. One example of a suitable film is an apertured three-layer elastomeric film of PE-SEBS-PE.

The total basis weight of the laminate is preferably 100 $g/m^2$ or less, more preferably no more than 90 $g/m^2$.

The elastic laminate 11 may be manufactured according to the method disclosed in WO 03/047488, wherein one spunbond layer 12a is applied to the film 13 in a tacky state and will thus bond to the film layer, while the other spunbond layer 12b is adhesively laminated to the film layer 13, using for example a pressure sensitive hot melt adhesive. Alternatively the laminate is manufactured according to a modified version of this known method, wherein the modification involves that the laminate is incrementally stretched (through intermeshing gears, IMG), to a point below the elongation at peak load of at least one of the non-elastic nonwoven layers to retain some strength for at least one of the nonwoven layers. The other layer may also be stretched to a point below its elongation at peak load, or to a point at which it will tear during stretching.

The method disclosed in WO 03/047488 involves stretching of the laminate above the point of failure of the fibrous material, so that the non-elastic layers break completely. Therefore, as described in WO 03/047488, the elongation of the laminate is not limited by the stretch modulus of the non-elastic material.

According to the modified method at least one, preferably both fibrous layers, which are bound to the elastic film are not, in contrast to the method described in WO 03/047488, completely torn upon manufacture of a laminate according to the present invention. Selection of fibrous materials which have an elongation at maximum load greater than the elasticity of the elastic laminate allows the elastic film to stretch without being hindered by the fibrous layers. Such a selection also ensures that the fibrous layers contribute to the puncture resistance of the laminate, as they are not completely torn or broken during manufacture. Preferably the fibrous layers, or at least one of the fibrous layers have an elongation at maximum load that is at least 10% higher than the elasticity of the laminate. This is described in more detail in PCT/SE2004/001005, which is incorporated herein by reference.

The opacity of a material layer is the characteristic ability of the material layer to visually hide from view an underlying object or pattern. The opacity is measured in %, wherein 100% opacity means that nothing can be seen through the material layer and 0% means that the material layer is completely transparent. The opacity is measured by the Opacity Test described below, which is based on luminous-reflectance-factor data.

Opacity of the laminate can be obtained by the incorporation of opacifying fillers into the laminate, particularly into the elastic film. Such pigments can be organic or inorganic dyes, colouring agents, or whitening agents. Inorganic materials such as titanium dioxide, inorganic carbonates, synthetic carbonates, talc, nepheline syenite, magnesium hydroxide, aluminium trihydrate siatomaceous earth, mica, natural or synthetic silicas, calcinated clays and mixtures thereof are preferred examples of opacifying fillers.

The filler is preferably added as a master batch at the extrusion of the film. One example of an appropriate concentration is about 5% filler by weight of the film.

It is further preferred that the elastic laminate 11 has a breathability (Water Vapour Transmission Rate) according to ASTM E96-00 Procedure D of at least 1500 $g/m^2$ 24 h, preferably at least 3000 $g/m^2$ 24 h.

The open area of the elastic film layer is preferably at least 5%, more preferably at least 8%. The open area is measured by image analysis methods and is defined as the sum of the hole area divided by the total area of the film sample.

Absorbent Core

The absorbent core 2 can be of any conventional kind. Examples of commonly occurring absorbent materials are cellulosic fluff pulp, tissue layers, highly absorbent polymers (so called superabsorbents), absorbent foam materials, absorbent nonwoven materials or the like. It is common to combine cellulosic fluff pulp with superabsorbents in an absorbent body. It is also common to have absorbent bodies comprising layers of different material with different properties with respect to liquid receiving capacity, liquid distribution capacity and storage capacity. The thin absorbent bodies, which are common in for example baby diapers and incontinence guards, often comprise a compressed mixed or layered structure of cellulosic fluff pulp and superabsorbent. The size and absorbent capacity of the absorbent core may be varied to be suited for different uses such as for infants or for incontinent adults.

Pant Diaper

The pant diaper disclosed in FIG. 1 is intended to enclose the lower part of the wearer's trunk like a pair of absorbent pants. It comprises a core region 3 located in the narrow crotch portion 19 of the article and extending into the front 5 and back regions 6 of the absorbent pants. A chassis region 4 surrounds the core region 3. The core region 3 is defined as the surface area of the article which is occupied by the absorbent core 2 and the areas outside the core which are covered by the liquid-impervious backsheet 9. The chassis 4 comprises front 5, back 6 and waist regions 7 located outside the crotch region 3. The front 5 and back regions 6 are joined to each other along their longitudinal edges by ultrasonic welds 15, glue strings or the like.

Figure 2:
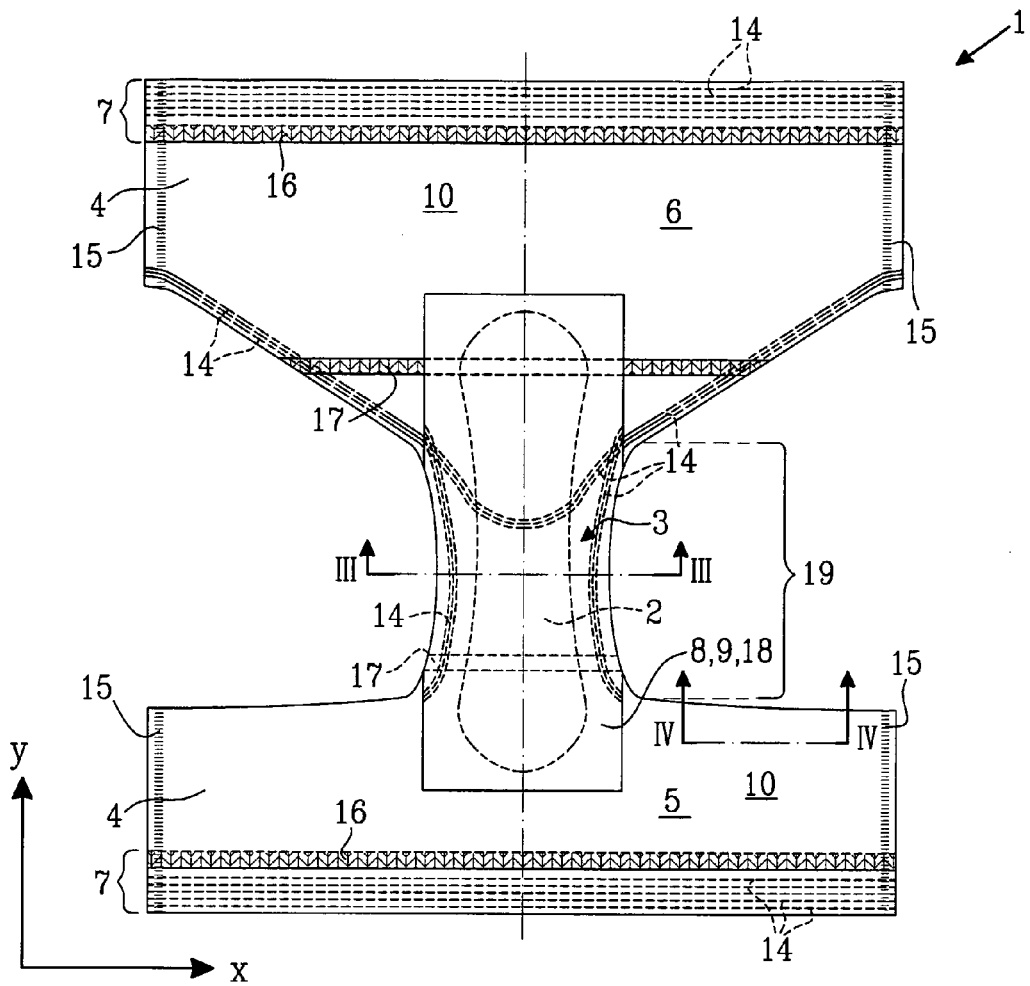
FIG. 2 shows is a simplified plan view of the pant diaper in its flat, uncontracted state prior to formation as seen from the body facing side.
Figure 3:
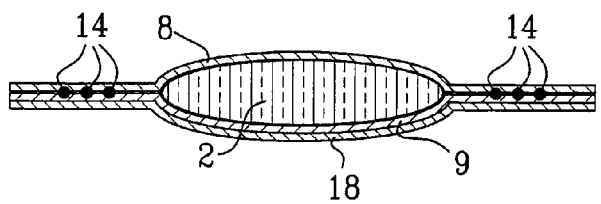
FIG. 3 is a cross section according to the line III-III in FIG. 2.
Figure 4:
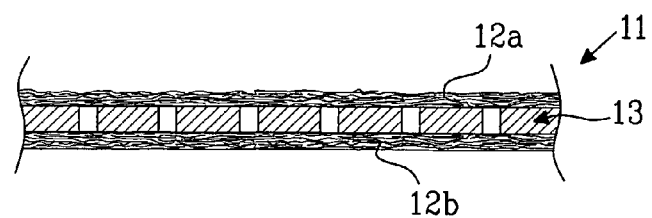
FIG. 4 is a cross section through an elastic laminate according to the invention according to the line IV-IV in FIG. 2.

According to one embodiment of the invention the surface area of the absorbent core 2 amounts to no more than 30% of the total surface area of the article, preferably no more than 20%, as measured in a flat state of the article. The term "flat state" herein means in an opened untensioned state, as seen in FIG. 2, and in which any tensioned elastic members have been deactivated.

The elastic web material 11 may cover the entire article, including the core region 3 and the entire chassis region 4. However according to a preferred embodiment a substantial part of the crotch portion 19 of the article is free from the elastic web material 11. A "substantial part" used herein refers to at least 50%, preferably at least 75%. Preferably also the waist region 7 of the chassis region is free from the elastic web material 11. The waist region 7 comprises a nonwoven material that is elasticized by elastic members 14, such as elastic threads, contractably affixed between material layers, such as nonwoven materials. Such elastic members 14 may also be arranged around the leg openings of the article. Ultrasonic welds 16, glue strings or the like, join the elastic laminate 11 to the elasticized nonwoven in the waist region 7.

The liquid-impervious backsheet material 9 underlies the absorbent core 2 and adjacent areas immediately outside the absorbent core 2. The area covered by the liquid-impervious backsheet 9 is defined as the core region 3. A nonwoven material 18 is arranged on the garment-facing side of the liquid-impervious backsheet 9 in the crotch portion of the article. The nonwoven material 18 is joined to the elastic web material 11 by means of ultrasonic welds 17, glue strings or the like. The elastic web material 11 and the liquid impervious backsheet overlap in the outer parts of the core region 3, as seen in FIG. 2, wherein the elastic web material 11 is arranged on the garment facing side of the liquid impervious backsheet 9.

The elastic web material 11 is preferably arranged as an outside coversheet material as well as inner coversheet material over at least a substantial part of the front region 5 of the chassis 4, which during use is intended to be applied against the stomach of the wearer, except for the waist region 7. A "substantial part" used herein means at least 50% of the surface area, preferably at least 75%, of the surface area of the front region 5 of the chassis 4. It is further preferred that the elastic web material 11 is arranged as an outside coversheet material as well as inner coversheet material over both the front 5 and back regions 6 of the chassis 4. Thus no additional backsheet or topsheet materials are required and the elastic web material constitutes the sole component of in these parts of the chassis 4. In at least 20%, preferably at least 25%, more preferably at least 30% and most preferably at least 40% of the total surface area of the article, as seen in a flat state according to FIG. 2, the elastic web material 11 constitutes the sole component of the chassis.

No additional elasticized side panels joining the front and back regions 5 and 6 are needed when using the elastic web material 11 according to the invention. If desired, additional elasticized side panels may of course be provided, especially in cases where the elastic web material 11 is arranged only in parts of the front and/or back regions.

As stated above the elastic web material 11 has an opacity of at least 40%, preferably at least 50% and more preferably at least 60%.

The opacity of the elastic web material provides a cloth-like appearance to the article, which is of particular importance when the article is a pant diaper. Especially in this case, where the elastic web material forms the sole component in considerable surface area regions of the pant diaper, such as large areas of the front and back regions, and the absorbent core covers only relatively small areas, 30% or less, of the article, the appearance of the elastic web material is of great importance for the overall appearance of the article. Thus by making the elastic web material opaque with an opacity of at least 40%, the pant diaper will appear more cloth-like and more like "normal" underwear, than if the elastic web material would have a higher degree of transparency.

It is further desired that the elastic web material has a puncture resistance of at least 15N as measured according to ASTM Designation D3763-02. Preferably, the elastic web material of the present invention has a puncture resistance of at least 20N, and more preferably at least 30N.

The elastic web material should preferably have a softness according to Kawabata of at least 20, preferably at least 30 and most preferably at least 40.

It is further desired that it has a formability according to Kawabata of no more than 50, preferably no more than 30, more preferably no more than 20 and most preferably no more than 10.

It is also desired that the elastic web material has a drapability according to Kawabata of no more than 40.

Description of Test Methods

Opacity

The opacity of the elastic web material is measured according to a slightly modified version of SS-ISO 2471:1998 by Swedish Standard Institute (Diffuse Reflectance Method). The method is originally intended for measuring the opacity for paper sheets, but it also functions well for measuring the opacity of other types of sheet materials, such as elastic laminates according to this invention. The opacity is measured in an unstretched condition of the elastic web material. The principle of the test method is to measure the Single-Sheet Luminous Reflectance Factor, $R_0$, through a single sheet against a standardized black backing and the Intrinsic Luminous Reflectance Factor, $R_\infty$, against a completely opaque white backing. The opacity (%) is calculated from the formula $100 \cdot R_0 / R_\infty$.

The following modifications of the test method were made:
i) When measuring the Single-Sheet Luminous Reflectance Factor, $R_0$, a black velvet fabric was used as backing.
ii) When measuring the Intrinsic Luminous Reflectance Factor, $R_\infty$, the measurement was made on one single sheet of the elastic laminate against a white tile as backing.
iii) The CIE illuminant D65 (10°) was used instead of the CIE illuminant C) (2°).

The measured opacity values are mean values from five measurements.

Puncture Strength

Puncture strength is measured according to ASTM Designation D3763-02. From penetration impact-type tests, this method produces data of load versus displacement. The maximum load for each laminate is calculated.

Tensile strength (Reference: ASTM D 882)

The method measures tensile strength and elongation of difference elastic materials. The tensile strength and elongation of a well-defined test piece is tested by means of a tensile tester.

Apparatus: Instron 4301
Tensile tester connected to a computer
Crosshead speed: 500 mm/min
Clamp distance: 50 mm Sample preparation: Test samples are cut from the entire width of the material. The width of the sample shall be 25.4 mm and the length at least 50 mm longer than the clamp distance if possible. It is of importance that the edges of the sample are even and without break notches. The samples are conditioned for at least 4 h in 50% RH±5% RH and 23° C.±2° C. before testing.

Procedure: The tensile tester is calibrated according to the apparatus instructions and set to zero. The sample is mounted and it is ensured that it is not obliquely or unevenly fastened. The material is prevented from slipping by using clamps covered with galloon or similar material. The tensile tester is started, and stopped after the material has broken (if not automatically controlled). Measurements resulting from premature failures (i.e. the sample breaks at the clamp, or is damaged during preparation) are ignored if possible.

The following results are expressed by the tensile tester/computer:

Maximum force, N/25.4 mm
Elongation at maximum force, %
Break force, N/25.4 mm
Elongation at break force, %
Knee point, N/%
Elasticity Test The method measures how an elastic material behaves at repeated load and unload cycles. The sample is stretched to a predetermined elongation and a cyclic movement between 0 and said predetermined elongation is performed. Desired load and unload forces are recorded. The permanent, i.e. remaining, elongation of the relaxed material is measured.

A tensile tester, Lloyd LRX, able to perform cyclic movements and equipped with a printer/plotter or software presentation is used. The sample is prepared by cutting it to a width of 25 mm and a length that is preferably 20 mm longer than the distance between the clamps in the tensile tester.

The tensile tester is calibrated according to the apparatus instructions. The parameters needed for the test (load and unload forces) are adjusted to:

Crosshead speed: 500 mm/min
Clamp distance: 50 mm
Preload: 0.05 N

The sample is placed in the clamps according to the marks and it is made sure that the sample is centred and fastened perpendicularly in the clamps. The tensile tester is started and three cycles between 0 and the predetermined elongation, equal to the highest defined $1^{st}$ load, are performed. Before the last cycle, the sample is relaxed for 1 minute, then the permanent elongation is measured by stretching the sample until a force of 0.1 N is detected and the elongation is read.

The permanent elongation after relaxation should be less than 10% and is measured by the method above. Thus an elasticity of 30% is defined as that the laminate should have a permanent relaxation after elongation of less than 10% after being exerted to an elongation of 30% in the tensile tester above. An elongation of 30% means an elongation to a length that is 30% longer than the initial length of the sample.

Kawabata Tests

The Kawabata KES-FB test is a Japanese quality judgment system used for textile materials and is disclosed in "The Standardization and Analysis of Hand Evaluation (2nd Edition), Sueo Kawabata, July 1980, The Hand Evaluation and Standardization Committee, The Textile Machinery Society of Japan". The test used in this invention uses two of the Kawabata testing machines, KES-FB2 for measuring Bending rigidity, B (gf·cm$^2$/cm), and KES-FB1 for measuring Shear stiffness, G (gf/cm·degree) and Tensile strain, EMT (%).

Bending Rigidity (B) KES-FB2

The slope was measured between 0.5 cm$^{-1}$ and 1.5 cm$^{-1}$ and −0.5 cm$^{-1}$ and −1.5 cm$^{-1}$.

The measurements were performed in both directions (MD and CD) with the following settings:

Total sample area: 20×20 cm;
Maximum curvature: Kmax=±2.5 cm$^{-1}$;
Bending rate: 0.5 cm$^{-1}$/sec;
Sample effective dimension: 20 cm length and 1 cm width;
Bending deformation is applied to the width direction.

Shear Stiffness (G) KES-FB1

The slope was measured between 0.5 cm$^{-1}$ and 2.5 cm$^{-1}$ and −0.5 cm$^{-1}$ and −2.5 cm$^{-1}$.

The measurements were performed in both directions (MD and CD) with the following settings:

Total sample area: 20×20 cm;
Tension of specimen: W=W=10 gf/cm;
Maximum shear angle: σ=±8°.
Sample effective dimension: 20 cm width and 5 cm length;
Shear deformation is applied to the width direction.

Tensile Strain (EMT)

The measurements were performed in both directions (MD and CD) with the following settings:

Total sample area: 20×20 cm;
Maximum load: Fm=500 gf/cm;
Tensile speed: 0.2 mm/sec.
Sample effective dimension: 20 cm width and 2.5 cm length;
Tensile deformation is applied to the length direction.
Elongation sens 50 mm/10V.

Softness (S)

The Softness (S) according to Kawabata is obtained from the formula:

$$S=\sqrt{EMT/B}$$

Formability (F)

The Formability (F) according to Kawabata is obtained from the formula:

$$F=B \cdot EMT.$$

Drapability (D)

The Drapability (D) according to Kawabata is obtained from the formula:

$$D=116+25 \cdot \log(B \cdot G/W)\text{, wherein }W\text{ is the basis weight of the sample.}$$

EXAMPLE

Opacity

The opacity of an elastic laminate sample was measured. The sample was an elastic laminate according to the invention comprising an inner apertured three-layer elastic film of PE-SEBS-PE, basis weight 36 g/m$^2$ and two outer layers of spunbond material, PP (polypropylene), each having a basis weight of 22 g/m$^2$. The laminate is produced by a modified version of the method disclosed in WO 03/047488 and which is described above, wherein one spunbond layer is applied to the film in a tacky state and will thus bond to the film layer, while the other spunbond layer is adhesively laminated to the film layer using for example a pressure sensitive hot melt adhesive (glue amount 3 g/m²). The laminate is incrementally stretched, at which the non-elastic spunbond layers are stretched to a point below the elongation at maximum load to retain some strength in the spunbond layers. The elasticity of the laminate after stretching is close to the elasticity of the elastic film layer.

The above-mentioned basis weights of the layers refer to the finished laminate after stretching. Before stretching the basis weight of the individual layers were: inner film layer 40 g/m², outer spunbond layers 25 g/m² each and glue layer 3 g/m². Since it is difficult to measure the basis weights of the individual layers after lamination and stretching an approximation has been made from the basis weights of the layers before lamination and stretching. The laminate before stretching had a total basis weight before stretching of 93 g/m² and after stretching it had a basis weight of 85 g/m², which means a deformation of about 10%. It is then assumed that the deformation of the individual fibrous layers and the film layer is the same, i.e. about 10%.

The inner film layer contained 4.9% by weight filler in the form of $TiO_2$. The open area of the film layer was 13%.

The opacity of the laminate was about 68%.

An opacity value of at least 40% is acceptable in order to provide the desired cloth-like appearance of the pant diaper disclosed above, which in considerable areas of the chassis contains the elastic laminate as the sole component. Preferably the opacity should be at least 50%, more preferably at least 60%.

It is further desired, for example for cost reasons, to have a low basis weight of the elastic laminate. The basis weight should be 100 g/m² or lower. The ratio Opacity/Basis Weight is therefore also an aspect of this invention. Preferably this ratio should be at least 0.4, more preferably at least 0.5 and most preferably at least 0.6, wherein opacity is measured in % and the basis weight is measured in g/m².

Puncture Resistance

The puncture resistance of three different samples (A, B and C) were measured according to ASTM Designation D3763-02 and are shown in Table 1.

Tensile Strength

The puncture resistance of three different samples (A, B and C) were measured according to the method given above and are shown in Table 1.

Elasticity

The elasticity of three different samples (A, B and C) were measured according to the method given above and are shown in Table 1.

Sample A is an elastic laminate according to WO03/047488 with 15 g/m² PP spunbond nonwoven on both sides of a 40 gsm elastic film. The used spunbond nonwoven has an elongation at maximum load of 60%, which is less than the elasticity of the laminate. The low puncture resistance of this material means that it falls outside the preferred values claimed in this application.

Sample B is an elastic laminate with 25 g/m² PP/PE spunbond nonwoven on both sides of a 36 g/m² elastic film.

Sample C is an elastic laminate with one layer of 25 g/m² PP/PE nonwoven and one layer of 20 g/m² PP/PE nonwoven on opposite sides of a 36 g/m² elastic film.

TABLE 1

|  | Sample A | Sample B | Sample C |
|---|---|---|---|
| Puncture force (N) | 12.8 | 49.5 | 40.6 |
| Basis weight (g/m²) | 78.66 | 87.96 | 82.71 |
| Tensile strength and Elongation MD (machine direction) | | | |
| Tensile strength at Peak (MD), N/25 mm | 8.29 | 25.3 | 28.03 |
| Elongation at break, % | 269.82 | 311.94 | 691.47 |
| Elongation at Peak/Deformation, % | 136 | 111.44 | 109.28 |
| CD (cross direction) | | | |
| Tensile strength at Peak (CD), N/25 mm | 11.72 | 11.15 | 9.16 |
| Elongation at break, % | 792.87 | 768.19 | 160.15 |
| Elongation at Peak/Deformation, % | 74.88 | 124.82 | 134.42 |
| Determination of load & unload forces and permanent elongation | | | |
| Tensile strength at 80% elongation (1$^{st}$ cycle) | 2.78 | 7.11 | 10.66 |
| Permanent Elongation (3$^{rd}$ cycle) | 7.86 | 7.52 | 8.09 |
| 3$^{rd}$ Retraction Forces | | | |
| At 80%, N/25 mm | 1.14 | 1.44 | 1.42 |
| At 60%, N/25 mm | 0.82 | 0.85 | 0.8 |
| At 40%, N/25 mm | 0.54 | 0.53 | 0.48 |

Kawabata Tests

Four different samples were measured in a Kawabata test with respect to Bending rigidity (B), Shear stiffness (G) and Tensile strain (EMT). From these measured values the Softness (S), Formability (F) and Drapability (D) were calculated.

The four samples were:

Sample laminate (SL): an elastic laminate as disclosed with respect to the Opacity test above.

Ref. 1: Cotton-knitted goods, so called jersey with elastic threads.

Ref. 2: Outer coversheet of Tena Discreet incontinence pant (odour control, size medium) produced by SCA Hygiene Products AB. The outer coversheet comprises two layers of nonwoven with parallel elastic threads there between, which wrinkle the material.

Ref. 3: Outer coversheet material of Poise normal super incontinence pant produced by Kimberly-Clark. The outer coversheet comprises two layers of nonwoven with parallel elastic threads there between which wrinkle the material.

A climate conditioning of the materials were performed at 20° C. and 65% RH for 48 hours. For the pant products, the absorbent core was removed and the outer coversheet was stretched over a knitwear measuring device for 24 hours and was then allowed to relax in the same climate during 24 hours.

The sizes of the samples were 10×10 cm.

All tests were made on three samples and in two material directions (machine direction, MD, and cross direction, CD).

The following results were obtained.

TABLE 2

| Sample | B, Bending rigidity (gf · cm²/cm) | | | G, Shear stiffness (gf/cm · degree) | | | EMT, Tensile strain (%) | | |
|---|---|---|---|---|---|---|---|---|---|
|  | MD | CD | Mean | MD | CD | Mean | MD | CD | Mean |
| SL | 0.095 | 0.022 | 0.059 | 1.46 | 1.38 | 1.42 | 208.4 | 92.0 | 150.2 |
| Ref. 1 | 0.03 | 0.03 | 0.03 | 0.58 | 0.64 | 0.61 | 160.6 | 173.2 | 166.9 |

TABLE 2-continued

| Sample | B, Bending rigidity (gf·cm²/cm) | | | G, Shear stiffness (gf/cm·degree) | | | EMT, Tensile strain (%) | | |
|---|---|---|---|---|---|---|---|---|---|
| | MD | CD | Mean | MD | CD | Mean | MD | CD | Mean |
| Ref. 2 | 1.05 | 0.09 | 0.57 | 0.87 | 0.68 | 0.77 | 23.9 | 211.7 | 117.8 |
| Ref. 3 | 1.53 | 0.04 | 0.78 | 1.74 | 1.21 | 1.47 | 26.28 | 195.3 | 110.8 |

From these results the Softness (S), the Drapability (D) and the Formability (F) according to Kawabata were calculated according to the formulas stated above. These results are stated in Table 3 below.

TABLE 3

| Sample | Softness (S) $\sqrt{EMT/B}$ | Drapability (D) $116 + 25 \log (B \cdot G/W)$ | Formability (F) $B \cdot EMT$ | Basis Weight (W) g/m² |
|---|---|---|---|---|
| SL | 50 | 40 | 9 | 88 |
| Ref. 1 | 75 | 13 | 5 | 231 |
| Ref. 2 | 14 | 45 | 67 | 160 |
| Ref. 3 | 12 | 51 | 87 | 133 |

The results should be interpreted in the following way:
Softness (S): a higher value indicates a softer material.
Drapability (D): a higher value indicates a stiffer material.
Formability (F): a higher value indicates that the material is less formable.

The test laminate according to the invention has a Softness (S) and a Formability (F) according to Kawabata which is close to cotton-knitted goods (Ref. 1). Also the Drapability (D) according to Kawabata is closer to the cotton-knitted reference material than the other two tested materials, used as outer coversheets on conventional incontinence pants. Thus the use of the elastic laminate as outer coversheet material in at least a part of the chassis region of the absorbent pant provides a pant article having a cloth-like feeling close to a cotton material. The pant will also have an excellent comfort and fit to the wearer's body. By using the elastic laminate only in those parts of the pant in which the properties of the material is best utilized, a very economic utilization of the material is accomplished.

As described above it is further understood that other types of elastic web materials, than the laminate described above, may be used, such as elastic nonwoven materials, nonwoven materials which per se are inelastic, but which have been elastified by means of elastic threads etc. The elastic web materials may comprise one layer or two or more layers that have been laminated.

The invention claimed is:

1. A pant type absorbent article, said article comprising a core region with an absorbent core and a chassis surrounding the core region, said chassis comprising front, back and waist regions, while the core region is located at least in a crotch portion of the article, a liquid impermeable backsheet is arranged at least in the core region on the garment-facing side of the absorbent core and a liquid permeable topsheet is arranged at least in the core region on the wearer-facing side of the absorbent core, said article having a longitudinal and a transverse direction,
wherein said article in at least a part of the chassis region comprises an outer coversheet in the form of an elastic web material constituting the sole component of the chassis in at least 20% of the total surface area of the article, said elastic web material having an opacity of at least 40% and a basis weight of no more than 100 g/m²,
wherein the elastic web material is a laminate composed of first and second layers of fibrous material and an elastic film layer located between said first and second fibrous layers, and
wherein at least one of the layers of fibrous material has an elongation at maximum load greater than the elasticity of the elastic laminate.

2. The absorbent article as claimed in claim 1, said elastic web material has an opacity of at least 50%.

3. The absorbent article as claimed in claim 1, wherein said elastic film layer contains an opacifying filler.

4. The absorbent article as claimed in claim 3, wherein the opacifying filler is selected from the group consisting of organic and inorganic dyes, colouring agents and whitening agents.

5. The absorbent article as claimed in claim 3, wherein the opacifying filler is selected from the group consisting of titanium dioxide, inorganic carbonates, synthetic carbonates, talc, nepheline syenite, magnesium hydroxide, aluminum trihydrate diatomaceous earth, mica, natural or synthetic silicas, calcinated clays and mixtures thereof.

6. The absorbent article as claimed in claim 1, wherein both layers of fibrous material have an elongation at maximum load greater than the elasticity of the elastic laminate.

7. The absorbent article as claimed in claim 1, wherein at least one of the layers of fibrous material have an elongation at maximum load of at least 10% greater than the elasticity of the elastic laminate.

8. The absorbent article as claimed in claim 1, wherein said elastic film layer is breathable.

9. The absorbent article as claimed in claim 8, wherein said elastic laminate has a Water Vapour Transmission Rate according to ASTM E96-00 Procedure D of at least 1500 g/m² 24 h.

10. The absorbent article as claimed in claim 8, wherein the elastic film layer has an open area of at least 5%.

11. The absorbent article as claimed in claim 1, wherein the first and/or the second layers of fibrous material comprise a mixture of polypropylene and polyethylene polymers.

12. The absorbent article as claimed in claim 1, wherein said elastic laminate comprises first and second fibrous layers of spunbond material, each having a basis weight of between 10 and 35 g/m², and a breathable elastic film layer having a basis weight between 20 and 80 g/m², said elastic laminate having a Water Vapour Transmission Rate according to ASTM E96-00 Procedure D of at least 1500 g/m² 24 h.

13. The absorbent article as claimed in claim 1, wherein the elastic web material has a basis weight of no more than 90 g/m².

14. The absorbent article as claimed in claim 1, wherein the elastic web material has an opacity (%)/basis weight (g/m²) ratio of at least 0.4.

15. The absorbent article as claimed in claim 1, wherein the elastic web material constitutes the sole component of the chassis in at least 25% of the total surface area of the article.

16. The absorbent article as claimed in claim 1, wherein said elastic web material has an elasticity in the transverse direction of the article of at least 30% when measured according to the elasticity test specified in the description.

17. The absorbent article as claimed in claim 16, wherein the elastic web material has an elasticity in the longitudinal direction of the article of at least 20% when measured according to the elasticity test specified in the description.

18. The absorbent article as claimed in claim 1, wherein said elastic web material has Softness (S) according to Kawabata of at least 20.

19. The absorbent article as claimed in claim 1, wherein said elastic web material has a Formability (F) according to Kawabata of no more than 50.

20. The absorbent article as claimed in claim 1, wherein said elastic web material has a Drapability (D) according to Kawabata of no more than 40.

21. The absorbent article as claimed in claim 1, wherein a part of the crotch portion of the article is free from said elastic web material.

22. The absorbent article as claimed in claim 1, wherein the waist region of the chassis is free from said elastic web material.

23. The absorbent article as claimed in claim 1, wherein the surface area of the absorbent core amounts to no more than 30% of the total surface area of the article, as measured in a flat state of the article.

24. The absorbent article as claimed in claim 1, wherein the article is a pull-up pant product comprising an elasticized waist region, which is free from said elastic web material, a crotch portion which is also free from said elastic web material and wherein the elastic web material is arranged as a sole component of the chassis in at least a substantial part of the front region of the article, which in use is intended to be applied over the stomach of the wearer.

25. The absorbent article as claimed in claim 1, wherein at least one of the layers of fibrous material have an elongation at maximum load of at least 20% greater than the elasticity of the elastic laminate.

26. The absorbent article as claimed in claim 8, wherein said elastic laminate has a Water Vapour Transmission Rate according to ASTM E96-00 Procedure D of at least 3000 g/m$^2$ 24 h.

27. The absorbent article as claimed in claim 8, wherein the elastic film layer has an open area of at least 8%.

28. The absorbent article as claimed in claim 1, wherein said elastic laminate comprises first and second fibrous layers of spunbond material, each having a basis weight of between 15 and 25 g/m$^2$, and a breathable elastic film layer having a basis weight between 20 and 60 g/m$^2$, said elastic laminate having a Water Vapour Transmission Rate according to ASTM E96-00 Procedure D of at least 3000 g/m$^2$ 24 h.

29. The absorbent article as claimed in claim 1, wherein the elastic web material has an opacity (%)/basis weight (g/m$^2$) ratio of at least 0.6.

30. The absorbent article as claimed in claim 1, the elastic web material constitutes the sole component of the chassis in at least 40% of the total surface area of the article.

31. The absorbent article as claimed in claim 1, said elastic web material has an elasticity in the transverse direction of the article of at least 70% when measured according to the elasticity test specified in the description.

32. The absorbent article as claimed in claim 1, wherein said elastic web material has Softness (S) according to Kawabata of at least 40.

33. The absorbent article as claimed in claim 1, wherein said elastic web material has a Formability (F) according to Kawabata of no more than 20.

34. The absorbent article as claimed in claim 1, wherein the elastic laminate is obtained by: (i) bonding the first layer of fibrous material to the elastic film layer by applying the first layer to the elastic film layer without adhesive while the elastic film layer is in a tacky state, (ii) adhesively laminating the second layer of fibrous material to the elastic film layer, and (iii) optionally incrementally stretching the laminated obtained after (i) and (ii) to a point below elongation at peak load of at least one of the fibrous layers so that the fibrous layer is partially torn.

35. A pant type absorbent article, said article comprising:
a core region with an absorbent core and a chassis surrounding the core region, said chassis comprising front, back and waist regions, while the core region is located at least in a crotch portion of the article,
a liquid impermeable backsheet is arranged at least in the core region on the garment-facing side of the absorbent core, and
a liquid permeable topsheet is arranged at least in the core region on the wearer-facing side of the absorbent core,
said article having a longitudinal and a transverse direction,
said article in at least a part of the chassis region comprises an outer coversheet in the form of an elastic web material in at least 20% of the total surface area of the article, said elastic web material having an opacity (%) to basis weight (g/m$^2$) ratio of at least 0.4,
wherein the elastic web material is a laminate composed of first and second layers of fibrous material and an elastic film layer located between said first and second fibrous layers, and
wherein at least one of the layers of fibrous material has an elongation at maximum load greater than the elasticity of the elastic laminate.

36. The absorbent article as claimed in claim 35, wherein the elastic laminate is obtained by: (i) bonding the first layer of fibrous material to the elastic film layer by applying the first layer to the elastic film layer without adhesive while the elastic film layer is in a tacky state, (ii) adhesively laminating the second layer of fibrous material to the elastic film layer, and (iii) optionally incrementally stretching the laminated obtained after (i) and (ii) to a point below elongation at peak load of at least one of the fibrous layers so that the fibrous layer is partially torn.

37. A pant type absorbent article, said article comprising:
a core region with an absorbent core and a chassis surrounding the core region, said chassis comprising front, back and waist regions, while the core region is located at least in a crotch portion of the article,
a liquid impermeable backsheet is arranged at least in the core region on the garment-facing side of the absorbent core, and
a liquid permeable topsheet is arranged at least in the core region on the wearer-facing side of the absorbent core,
said article having a longitudinal and a transverse direction,
said article in at least a part of the chassis region comprises an outer coversheet in the form of an elastic web laminate material in at least 20% of the total surface area of the article, said elastic web laminate material having a layer of apertured elastic film having a basis weight between 20 and 80 g/m$^2$, and an opacity (%) to basis weight (g/m$^2$) ratio of at least 0.4, wherein the elastic web material is a laminate composed of first and second layers of fibrous material and an elastic film layer located between said first and second fibrous layers, and wherein at least one of the layers of fibrous material has an elongation at maximum load greater than the elasticity of the elastic laminate.

38. The absorbent article as claimed in claim 37, wherein said apertured elastic film has an open area of at least 5%.

39. The absorbent article as claimed in claim 37, wherein the elastic laminate is obtained by: (i) bonding the first layer of fibrous material to the elastic film layer by applying the first layer to the elastic film layer without adhesive while the elastic film layer is in a tacky state, (ii) adhesively laminating the second layer of fibrous material to the elastic film layer, and (iii) optionally incrementally stretching the laminated obtained after (i) and (ii) to a point below elongation at peak load of at least one of the fibrous layers so that the fibrous layer is partially torn.

40. A pant type absorbent article, said article comprising:
a core region with an absorbent core and a chassis surrounding the core region, said chassis comprising front, back and waist regions, while the core region is located at least in a crotch portion of the article,
a liquid impermeable backsheet is arranged at least in the core region on the garment-facing side of the absorbent core, and
a liquid permeable topsheet is arranged at least in the core region on the wearer-facing side of the absorbent core,
said article having a longitudinal and a transverse direction,
said chassis region including an outer coversheet in the form of an elastic web material in at least 20% of the total surface area of the article,
said elastic web material having an opacity of at least 40% and a Water Vapour Transmission Rate according to ASTM E96-00 Procedure D of at least 1500 g/m$^2$ 24 h,
wherein the elastic web material is a laminate composed of first and second layers of fibrous material and an elastic film layer located between said first and second fibrous layers, and
wherein at least one of the layers of fibrous material has an elongation at maximum load greater than the elasticity of the elastic laminate.

41. The absorbent article as claimed in claim 40, wherein the elastic laminate is obtained by: (i) bonding the first layer of fibrous material to the elastic film layer by applying the first layer to the elastic film layer without adhesive while the elastic film layer is in a tacky state, (ii) adhesively laminating the second layer of fibrous material to the elastic film layer, and (iii) optionally incrementally stretching the laminated obtained after (i) and (ii) to a point below elongation at peak load of at least one of the fibrous layers so that the fibrous layer is partially torn.

* * * * *